United States Patent [19]

Yamanaka et al.

[11] Patent Number: 5,558,861

[45] Date of Patent: Sep. 24, 1996

[54] MODIFIED MICROBIALLY-PRODUCED CELLULOSE GEL WITH HUMAN EPIDERMAL CELLS ADSORBED THEREON FOR USE AS A SKIN GRAFT OR VULNERARY COVER

[75] Inventors: Shigeru Yamanaka; Yuzuru Eto; Satoshi Takano; Kunihiko Watanabe; Hiroshiro Shibai, all of Kawasaki, Japan

[73] Assignee: Ajinomoto Co., Inc., Tokyo, Japan

[21] Appl. No.: 567,212

[22] Filed: Dec. 5, 1995

Related U.S. Application Data

[63] Continuation of Ser. No. 407,250, Mar. 20, 1995, abandoned, which is a continuation of Ser. No. 281,135, Jul. 27, 1994, abandoned, which is a continuation of Ser. No. 159,708, Dec. 1, 1993, abandoned, which is a continuation of Ser. No. 44,083, Apr. 6, 1993, abandoned, which is a continuation of Ser. No. 653,473, Feb. 11, 1991, abandoned, which is a continuation of Ser. No. 39,739, Apr. 20, 1987, abandoned.

[30] Foreign Application Priority Data

Apr. 22, 1986 [JP] Japan ................................. 61-92479
Jul. 18, 1986 [JP] Japan ................................. 61-169554

[51] Int. Cl.⁶ ...................... A01N 63/00; A61F 13/00; A61F 2/10; A61L 15/00; A61K 9/14; A61K 35/36; C08B 1/00; C12N 1/02

[52] U.S. Cl. .................. 424/93.7; 424/93.1; 424/422; 424/445; 424/488; 424/574; 623/15; 536/56; 435/1.1 W; 435/240.2; 435/240.23; 435/240.243; 435/948

[58] Field of Search ................... 435/1, 240.2, 240.23, 435/240.241, 240.243, 948; 623/15; 536/56; 424/93.1, 93.7, 422, 445, 488, 574

[56] References Cited

U.S. PATENT DOCUMENTS

| 4,036,693 | 7/1977 | Levine et al. ................... 435/240.24 |
| 4,464,468 | 8/1984 | Avrameas et al. ................ 435/179 |

FOREIGN PATENT DOCUMENTS

| 2059991 | 4/1981 | United Kingdom . |
| 8001350 | 7/1980 | WIPO . |
| 86022095 | 4/1986 | WIPO . |

OTHER PUBLICATIONS

Talbot et al, "Utilisation of DEAE–cellulose as a microcarrier material", CA93, # 67435j 1985.
Reuveny et al, "Newly developed microcarrier culturing systems" CA. 104, # 107787e Mar., 1986.
Patent Abstracts of Japan, vol. 10, No. 178 (C–355) [2234] Jun. 21, 1988.

Primary Examiner—Chhaya D. Sayala
Assistant Examiner—Susan M. Dadio
Attorney, Agent, or Firm—Oblon, Spivak, McClelland, Maier, & Neustadt, P.C.

[57] ABSTRACT

Disclosed is a gel of microbially-produced cellulose, characterized in that the microbially-produced cellulose is modified by (1) physically or chemically bonding an animal cell adhesive protein to the cellulose, and/or (2) substituting hydrogen atoms of at least parts of hydroxyl groups of the cellulose with a positively or negatively charged organic group. This gel is valuable as a carrier for mass culture of animal cells or as a medical vulnerary cover.

7 Claims, No Drawings

MODIFIED MICROBIALLY-PRODUCED CELLULOSE GEL WITH HUMAN EPIDERMAL CELLS ADSORBED THEREON FOR USE AS A SKIN GRAFT OR VULNERARY COVER

This application is a Continuation of application Ser. No. 08/407,250, filed on Mar. 20, 1995, now abandoned, which is a continuation of application Ser. No. 08/281,135, filed on Jul. 27, 1994, now abandoned, which is a continuation of application Ser. No. 08/159,708, filed Dec. 1, 1993, now abandoned, which is a continuation of application Ser. No. 08/044,083, filed Apr. 6, 1993, now abandoned, which is a continuation of application Ser. No. 07/653,473, filed Feb. 11, 1991, now abandoned, which is a continuation of application Ser. No. 07/039,739 filed Apr. 20, 1987, now abandoned.

BACKGROUND OF THE INVENTION (1) Field of the Invention

The present invention relates to a gel of a microbially-produced cellulose, in which an animal cell adhesive protein is bonded to said cellulose or said cellulose is chemically modified.

This gel is valuable as a carrier for mass culture of animal cells or as a medical vulnerary cover. Especially, a complex comprising an animal cell bonded to or adsorbed in this gel is very valuable as a medical vulnerary cover.

(2) Description of the Related Art

The mass culture method using a carrier to which an animal cell is bonded is widely adopted.

As the material for the carrier, there can be mentioned plastics and glass for a sheet or plate carrier, crosslinked gelatin (Gell-Beads supplied by KC Biological Co., U.S.A.), charged group-added polyacrylamide (Biocarrier supplied by Bio-Rad Co., U.S.A.), polystyrene (Biosilon supplied by Nunc Co., Denmark), dextran (Superbeads supplied by Flow Labs Co., U.S.A.), cellulose granule (DE-52 supplied by Whatman Co., Great Britain) and collagen-coated dextran (Cytodex supplied by Pharmacia Co., Sweden) for a bead carrier, and cellulose acetate (supplied by Amicon Co., U.S.A.) for a hollow fiber carrier.

A protecting material for protecting an externally wounded or burnt skin at an accident or disaster, promoting regrowth of the epidermis, and healing the wound is called "vulnerary cover" or "artificial skin" (hereinafter referred to as "vulnerary cover").

Gauze has heretofore been used most widely as the vulnerary cover, but recently, lyophilized pig skin (LPS) having superior characteristics to gauze has been used. This is a living body material and in appearance resembles human skin. This material is soft and has a good adhesion to a wound and is superior in that it promotes regrowth of the skin.

Furthermore, a vulnerary cover composed of collagen has recently been marketed. This vulnerary cover is in the form of a non-woven fabric or film or is complexed with a silicone film, and is characterized in that it has no antigenic property and sterilization is possible.

Moreover, a complex of a polyamino acid film and a synthetic polymer film has been proposed as a vulnerary cover. This vulnerary cover is characterized in that it is not decomposed by a protease.

In addition, there is known a plasma film or fibrin film prepared from human blood. This film has an excellent absorbing property and is not irritating to the human body.

Still further, a vulnerary cover utilizing a film of a microbially-produced cellulose, which is different from an amino acid polymer or a protein, is proposed in British Patent No. 2,131,701.

Materials customarily used for carriers for mass culture of animal cells have problems in that the adhesion of animal cells and the propagation quantity of animal cells are insufficient. Moreover, a material capable of providing a sheet-shaped or plate-shaped carrier having an excellent softness and the like has not been developed.

Furthermore, materials heretofore used for vulnerary covers involve the following problems. A vulnerary cover formed of lyophilized pig skin or collagen is readily decomposed by a protease and is fused to cause contamination. Accordingly, it is necessary to frequently renew a vulnerary cover. A film of a polyamino acid is not decomposed by a protease, but the film must be supported by an appropriate support such as a silicone film and the manufacturing process is complicated. A plasma film or fibrin film prepared from human blood has excellent characteristics, but since the starting material is expensive, the film is not easily available. A film of a microbially-produced cellulose has problems in that the adhesion to epidermal cells is poor, the film is readily peeled from the wound to cause contamination, and regrowth of the skin is not promoted.

SUMMARY OF THE INVENTION

It is therefore a primary object of the present invention to solve the problems involved in the conventional materials and provide a microbially-produced cellulose gel suitable for the propagation of animal cells having an excellent adhesion to epidermal cells.

In accordance with one aspect of the present invention, there is provided a gel of a modified microbially-produced cellulose, which comprises a microbially-produced cellulose to which an animal cell adhesive protein is physically or chemically bonded and/or hydrogen atoms of at least parts of hydroxyl groups of which are substituted with a positively or negatively charged organic group.

In accordance with another aspect of the present invention, there is provided a complex comprising an animal cell adsorbed in or bonded to the above-mentioned modified microbially-produced cellulose gel.

In accordance with still another aspect of the present invention, there is provided a complex comprising a gel of an unmodified microbially-produced cellulose and an animal cell adsorbed in or bonded to said gel.

DESCRIPTION OF THE PREFERRED EMBODIMENTS

By the term "microbially-produced cellulose" we mean cellulose produced by a microbe. By the term "a gel of microbially-produced cellulose" we mean a solid colloidal solution of microbially-produced cellulose in a physiologically-acceptable liquid such as deionized water, saline or glycerol. A typical example of the physiologically-acceptable liquid is deionized water.

The microbially-produced cellulose can be obtained according to the following procedures.

Any of microbes belonging to the genera Acetobacter, Pseudomonas and Agrobacterium can be used as the cellulose-producing microbe. For example, there can be mentioned *Acetobacter aceti subspecies xylinum*, ATCC 10821.

In the present invention, production of the microbially-produced cellulose is accomplished by inoculating an ordinary nutrient culture medium comprising a carbon source, a nitrogen source, inorganic salts and, if necessary, organic trace nutrients such as amino acids and vitamins, with a cellulose-producing microbe, and allowing the culture medium to stand still or gently stirring the culture medium under aeration. As the carbon source, there can be mentioned glucose, sucrose, maltose, hydrolyzed starch and molasse. Furthermore, ethanol, acetic acid, citric acid or the like may be used alone or in combination with the above-mentioned carbon sources. As the nitrogen source, there can be used ammonium salts such as ammonium sulfate, ammonium chloride and ammonium phosphate, nitrates, urea and peptone. As the organic trace nutrient, there can be mentioned amino acids, vitamins, fatty acids and nucleic acids, and peptone, casamino acids, yeast extracts and soybean proteolysis products containing these trace nutrients. When a nutrient-requiring mutant requiring an amino acid or the like for the growth is used, it is necessary to add such nutrients. As the inorganic salt, there can be used a phosphoric acid salt, a magnesium salt, a calcium salt, an iron salt and a manganese salt.

Ordinary culturing conditions may be adopted. Namely, if culturing is carried out at a pH value of 2.5 to 9 and a temperature controlled at 20° to 40° C. for 1 to 30 days, a microbially-produced cellulose is obtained on the surface layer of the culture medium.

The so-obtained microbially-produced cellulose is in the form of a gel containing a large amount of water, which has a structure in which ribbon-shaped microfibrils having a width of 100 to 500 Å and a thickness of 10 to 200 Å are entangled with one another.

The water content of the microbe-produced cellulose is at least 95% (v/v). The microbially-produced cellulose is readily decomposed by a cellulase to form glucose. More specifically, when a suspension of the microbially-produced cellulose having a concentration of 0.1% (w/v) is prepared and is reacted at 30° C. for 24 hours with a 0.5% (w/v) solution of a cellulase (EC3.2.1.4 supplied by Amano Pharmaceutical Co.) in a 0.1M acetic acid buffer solution, it is seen that a part of the microbially-produced cellulose is decomposed. When the supernatant is developed and examined by the paper chromatography, glucose and small amounts of cellobiose, cellotriose and cellooligosaccharide are detected. In some cases, small amounts of fructose and mannose are additionally detected.

The kind of the microbially-produced cellulose used in the present invention is not particularly critical, so long as it has the foregoing properties.

Not only the microbially-produced cellulose isolated from the culture medium but also the microbially-produced cellulose containing certain impurities can be used in the present invention. For example, sugars left in the culture medium, salts and yeast extracts may be contained in the microbially-produced cellulose. Moreover, certain quantities of microbe cells may be contained in the microbially-produced cellulose.

The gel of the microbially-produced cellulose obtained by the fermentation process may be directly used as the cellulose after washing, or it may be used after the gel is disintegrated by application of a mechanical shearing force. The mechanical shearing means is not particularly critical, but disintegration can be easily accomplished by a rotary disintegrator, a mixer or the like.

The gel of the microbially-produced cellulose or the disintegrated gel may be once dried and then returned to a gel state. The drying method is not particularly critical, but drying must be carried out at temperatures which will not decompose the cellulose. Since the microbially-produced cellulose is composed of fine fibers having many hydroxyl groups on the surface, the fibers are adhered to one another during drying and the fibrous shape is lost. Accordingly, to prevent occurrence this phenomenon and retain the shape of fine fibers, it is preferable to adopt freeze drying or critical point drying.

The gel of the microbially-produced cellulose may be complexed with an appropriate auxiliary material for the purposes of reinforcement, change of the specific gravity, immobilization, modification of the affinity, prevention of exudation of the liquid component and the like. As the auxiliary material to be complexed, there can be mentioned non-woven fabrics and other fabrics composed of natural fibers such as cotton and wool or man-made fibers such as regenerated celluloses and polyesters, films, paper sheets and porous films of polyethylene, polyvinyl alcohol and silicone rubber, organic or inorganic granules of alumina, glass and crystalline celluloses, and water-soluble or polar solvent-soluble materials or hydrophilic gel-forming materials such as agar, dextran, polyacrylamide, polyvinylpyrrolidone, alginic acid salts, chitin, hyaluronic acid, curdlan, polyacrylic acid salts, pullulan, carrageenan, glucomannan, cellulose derivatives and polyethylene glycol.

The complexing method is roughly divided into a method in which culturing is carried out in the state where a substance to be complexed is incorporated in the culture medium and the microbially-produced cellulose is formed on the surface or in the interior of said substance, and a method in which the microbially-produced cellulose obtained in the form of a gel by culturing is impregnated or backed with a substance to be complexed or the gel film is disintegrated and then complexed with said substance.

An animal cell adhesive protein is physically or chemically bonded to the microbially-produced cell used in the present invention and/or the microbially-produced cellulose is chemically modified.

As the method for physically bonding the protein to the cellulose, there can be adopted a method in which the protein is adsorbed in the surface of the microbially-produced cellulose or the protein is gelled on the surface of the microbially-produced cellulose. For example, only by immersing the microbially-produced cellulose in a solution of the protein, the protein can be adsorbed in the cellulose. Moreover, a strong physical bonding can be formed by adsorbing the cellulose in a protein solution and gelling or solidifying the protein by changing the pH value, the temperature, the salt concentration, the metal ion concentration or the like. Specifically, in the case of collagen, it is sufficient if the pH value is changed, and in the case of gelatin, it is sufficient if the temperature is lowered. Crosslinking may be effected in the protein by using glutaraldehyde or transglutaminase.

In order to increase the bondability to the protein, the microbially-produced cellulose may be converted to an appropriate derivative by a conventional procedure, for example, by etherification, esterification, grafting, or deoxidation.

As the chemical bonding method, there is ordinarily adopted a method in which crosslinking is effected by using an epihalohydrin or cyanogen halide. Any method capable of forming a covalent bond or crosslinking between the polysaccharide substance and the protein may be adopted.

Any of proteins having a function of promoting the adhesion of the animal cell to the gel of the microbially-produced cellulose can be used as the protein to be bonded. For example, there can be used collagens of types I, II, III and IV, Atelocollagen (tradename, supplied by Koken K.K., Japan), fibronectin and laminin.

Chemical modification of the microbially-produced cellulose is accomplished by substituting hydrogen atoms of at least parts of hydroxyl groups of the cellulose with a positively or negatively charged organic group.

Introduction of a positively charged substituent is preferred for culturing animal cells. A substituent containing ammonia, at least one hydrogen of which is substituted with an alkyl group, that is, a substituent represented by the following formula (I) or (II), is preferred:

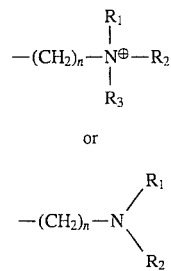

In the formulae (I) and (II), n is an integer of from 0 to 8, and $R_1$, $R_2$ and $R_3$ independently represent hydrogen atom, an alkyl group such as a methyl, ethyl or propyl group, an aryl group such as a phenyl or naphthyl group, an aralkyl group such as a benzyl group, an alkaryl group, a cycloalkyl group, or an alkoxyalkyl group, with the proviso that the case where all of $R_1$, $R_2$ and $R_3$ represent a hydrogen atom is excluded. The groups $R_1$, $R_2$ and $R_3$ may have an amino group, a hydroxyl group or the like bonded thereto.

As typical instances of the substituents represented by the formulae (I) and (II), there can be mentioned aminoalkyl groups such as an aminoethyl group, dialkylaminoalkyl groups such as a diethylaminoethyl group, trialkylaminoalkyl groups such as a triethylaminoethyl group, dialkylhydroxyalkylaminoalkyl groups such as a diethyl-(2-hydroxypropyl)-aminoethyl group, a substituent introduced by reacting the cellulose with an epihalohydrin and a trialcoholamine such as triethanolamine, a substituent introduced by reacting the cellulose with a quaternary halohydrin formed by reaction between an epihalohydrin and a tertiary amine or with a quaternary amine-containing epoxide, a guanidoalkyl group, a p-aminobenzyl group, and a benzoylated and/or naphthoylated dialkylaminoalkyl group.

Positively charged substituents other than those mentioned can be used, so far as they can be introduced into the cellulose. For example, there may be adopted a method in which the cellulose is weakly anionized and an appropriate cation, for example, polyethylene-imine, is adsorbed in the weakly anionized cellulose.

As the means for introducing a negatively charged substituent, there can be mentioned a method in which a carboxymethyl group, a carboxyethyl group, a phosphoric acid group or a sulfuric acid group is introduced.

The modified microbially-produced cellulose gel of the present invention can be used in various forms, but preferably, the gel is used in the form of a sheet-like or filmy shaped body.

The modified microbially-produced cellulose of the present invention can be used as a carrier for culturing animal cells inclusive of human epidermal cells, whereby animal cells can be cultured at a high density and a high propagation speed. Furthermore, the unmodified microbially-produced cellulose can be used as a carrier for culturing animal cells. As the animal cell to be cultured, there can be mentioned all of anchorage dependent cells of animals inclusive of human, and some anchorage independent (suspended) cells that can be bonded to the gel of the present invention.

A normal cell-culturing medium containing 0 to 50% of serum can be used for culturing these animal cells. An ordinary cell-culturing plastic petri dish or flask may be used as the culturing device, and if necessary, a spinner flask equipped with a rotor can be used.

Furthermore, the modified or unmodified microbially-produced cellulose gel can be used as a carrier for a mass culture of animal cells.

Accordingly, the microbially-produced cellulose gel can be utilized for the production of interferon by fibroblasts, interleukin-1 by mouse macrophages, a plasminogen activator by human fibroblasts, an oncolytic factor by human leukemia cells, a monochloral antibody by hybridoma cells, and other polypeptides.

Moreover a product obtained by culturing human epidermal cells substantially in the monolayer state on the sheet-shaped microbially-produced cellulose gel of the present invention is especially valuable as a vulnerary cover or artificial skin to be applied to the affected skin such as the burnt or wounded skin. This culture product can be obtained in a relatively short time, and it is sufficient if the sheet-shaped culture product is applied to the affected part so that the cell layer adheres to the affected part. The cell layer having an activity acts as the nucleus of the rebirth of the epidermis, and when the cellulose gel on the top surface is dried, an air-permeable and cell-impermeable porous protecting layer is formed. In the case where such an artificial skin is prepared and applied according to the conventional technique, a method must be adopted in which epidermal cells are cultured in multiple layers on a carrier over a long period (Howard Green and Olaniyi Kehinde, Proc, Natl, Acad, Sci, USA 1979, 76, 5665-8), the cultured cell layer is peeled from the carrier by a troublesome operation, the cell layer is applied to the skin so that peeled surface (the active side) of the cell layer adheres to the affected part, and the applied cell layer is covered with a protecting material such as a gauze pad.

The modified microbially-produced cellulose of the present invention is excellent as a medical vulnerary cover because the microbially-produced cellulose per se has excellent characteristics and has a high adhesion to animal cells added by modification and the modified microbially-produced cellulose has a high adhesion to the texture of the wounded part.

The present invention will now be described in detail with reference to the following examples.

EXAMPLE 1

A sterilized petri dish having a diameter of 15 cm was charged with 100 ml of a culture medium comprising 5 g/dl of sucrose, 0.5 g/dl of yeast extract (Difco), 0.5 g/dl of ammonium sulfate, 0.3 g/dl of $KH_2PO_4$ and 0.05 g/dl of $MgSO_4.7H_2O$ (pH=5.0), which had been steam-sterilized at 120° C. for 20 minutes.

The culture medium was inoculated with 2 platinum loops of *Acetobacter aceti subspecies xylinum* ATCC 10821 which had been grown at 30° C. for 7 days in a test tube slant agar culture medium formed by adding 2 g/dl of agar to the above-mentioned culture medium, and culturing was carried out at 30° C. When culturing was conducted for 2 weeks, a gel film having a thickness of about 2 mm and containing a cellulosic polysaccharide was formed on the culture liquid.

The so-obtained film was washed with water and immersed in a 20% aqueous solution of NaOH in an amount 20 times the weight of the film at 100° C. for 30 minutes. This immersion operation was further repeated 2 times. After the immersion operation, the film was neutralized with a 1N aqueous solution of HCl, and the gel film was washed in running water for one day and night.

After this washing, 200 g of the milky white transparent gel film (hereinafter referred to as "washed gel film" for brevity) was mixed with 200 g of water and 4 g of NaOH, and the mixture was allowed to stand at 70° C. for 1 hour with stirring. Then, a solution of 12 g of glycidyltrimethyl ammonium chloride in 40 ml of $H_2O$ was added to the liquid mixture and the cationization treatment was carried out at 70° C. for 5 hours. After the reaction, the alkali was neutralized with dilute hydrochloric acid, and the cationized gel film was washed with water.

The cationized gel film was cut into a disc having a diameter of 30 mm and heat-sterilized in a sufficient amount of water at 120° C. for 20 minutes. The sterilized cationized gel film was sufficiently equilibrated in (a) an MEM culture medium containing 10% of calf fetus serum, (b) Dulbecco's modified MEM culture medium, (c) an α-MEM culture medium or (d) an RPMI culture medium, and was then placed in a plastic petri dish having a diameter of 30 mm. The petri dish (a) was charged with 4 ml of an MEM culture medium containing 10% of calf fetus serum, in which $2\times10^5$ L-929 cells were suspended, or with 4 ml of an MEM culture medium containing 10% of calf fetus serum, in which $2\times10^5$ J-111 cells were suspended. The petri dish (b) was charged with 4 ml of Dulbecco's modified MEM culture medium containing 10% of calf fetus serum, in which $2\times10^5$ 3T3 Swiss albino cells were suspended, or with 4 ml of Dulbecco's modified culture medium containing 10% of calf fetus serum, in which $2\times10^5$ M-MSV-Balb/3T3 cells were suspended. The petri dish (c) was charged with 4 ml of an α-MEM culture medium containing 10% of calf fetus serum, in which $2\times10^5$ CHO cells were suspended, and the petri dish (d) was charged with 4 ml of an RPMI culture medium containing 10% of calf fetus serum, in which $2\times10^5$ THP-1 cells were suspended. Stationary culturing was carried out in a carbon dioxide gas incubator maintained at 37° C. for 5 days. After culturing, the cationized gel film was taken out and washed sufficiently with phosphate buffer saline, and the film was treated in a 3% solution of trypsin at 37° C. for 20 minutes and the cell layer was peeled from the surface of the gel film by using a rubber policeman. The number of living cells in the so-obtained cell suspension was measured according to the trypan blue dye exclusion test. The results are shown in Table 1.

TABLE 1

| Evaluation of Cationized Gel Film Obtained by Stationary Culture Method | | | |
|---|---|---|---|
| Cells | A | B | C |
| Anchorage Dependent Cells | | | |
| Mouse L-929 | $3.6 \times 10^6$ | $0.8 \times 10^5$ | $3.2 \times 10^6$ |
| Human J-111 | $2.1 \times 10^6$ | $0.8 \times 10^5$ | $1.7 \times 10^6$ |
| Mouse M-MSV-Balb/3T3 | $2.6 \times 10^6$ | $0.6 \times 10^5$ | $3.0 \times 10^6$ |
| Mouse 3T3 (Swiss albino) | $3.0 \times 10^6$ | $0.8 \times 10^5$ | $2.8 \times 10^6$ |
| Hamster CHO | $3.1 \times 10^6$ | $0.8 \times 10^5$ | $3.3 \times 10^6$ |

TABLE 1-continued

| Evaluation of Cationized Gel Film Obtained by Stationary Culture Method | | | |
|---|---|---|---|
| Cells | A | B | C |
| Anchorage Independent (Suspended) Cells | | | |
| Human THP-1 | 0 | $0.8 \times 10^5$ | $2.5 \times 10^6$ |

Note
A: the number of cells growing while adhering to the plastic petri dish having a diameter of 30 mm
B: the number of cells adhering to the uncationized washed gel film
C: the number of cells growing while adhering to the cationized gel film Each number was the number of cells per petri dish having a diameter of 30 mm.

EXAMPLE 2

The total nitrogen content of the cationized gel film obtained in Example 1 was determined according to the elementary analysis method and Kjeldahl method. The results are shown in Table 2.

TABLE 2

| | Elementary Analysis Method | Kjeldahl Method |
|---|---|---|
| N content in washed gel film before cationization | 0.15% | 0.13% |
| N content in gel film after cationization | 0.33% | 0.35% |

The washed gel film was dried, and the weight was measured. Then, the film was pulverized and the cationization was carried out under the same conditions as described in Example 1. The cationization product was then washed and dried, and the weight was measured. The obtained results are shown in Table 3.

TABLE 3

| | Weight |
|---|---|
| Dry product of washed gel film | 10.1855 g |
| Dry product of washed and cationized gel film | 10.4031 g |

From the foregoing results, it is seen that the substituent was introduced into about 0.8% of hydroxyl groups of the cellulose.

EXAMPLE 3

A Sakaguchi flask having a capacity of 500 ml was charged with 400 ml of a culture medium having the same composition as described in Example 1 and the culture medium was sterilized at 120° C. for 30 minutes. The culture medium was inoculated with 1 platinum loop of *Acetobacter aceti subspecies xylinum* ATCC 10821, and shaking culturing was carried out at 30° C. for 20 days to obtain a seed medium.

A glass bubble tower having a capacity of 500 ml and a diameter of 4 cm was sterilely charged with 350 ml of the above-mentioned culture medium and 50 ml of the seed medium was added. Culturing was conducted at 30° C. at an aeration rate of ⅓ V.V.M. for two weeks to obtain a granular pellet composed of a gelatinous cellulose, which had a diameter of 100 to 200 μm.

The granular pellet was washed and was cationized in the same manner as described in Example 1.

The so-prepared cationized granular pellet was suspended in a proper amount of distilled water and heat-sterilized at 120° C. for 20 minutes. The sterilized cationized granular pellet was recovered by using a centrifugal separator and was suspended in an MEM culture medium containing 10% of calf fetus serum, Dulbecco's modified MEM culture medium or an α-MEM culture medium. After sufficient equilibration, the cationized granular pellet was collected by a centrifugal separator. A spinner flask having a total volume of 90 ml was charged with $8\times10^5$ of so-collected cationized granular pellets, and the flask was charged with 20 ml of an MEM culture medium containing 10% of calf fetus serum, in which $1\times10^7$ L-929 cells were suspended, 20 ml of an MEM culture medium containing 10% of calf fetus serum, in which $1\times10^7$ J-111 cells were suspended, or 20 ml of Dulbecco's modified MEM culture medium containing 10% of calf fetus serum, in which $1\times10^7$ M-MSV-Balb/3T3 cells were suspended. Spinner culturing was carried out at 37° C. and 100 rpm for 5 days in the presence of carbon dioxide gas. After completion of culturing, some cationized granular pellets were sampled and the number of cells adhering to one granular pellet was measured by using an optical microscope. The obtained results are shown in Table 4.

TABLE 4

| Cell | A | B |
| --- | --- | --- |
| L-929 | $2.5 \times 10^6$ | $4.0 \times 10^6$ |
| J-111 | $1.8 \times 10^6$ | $2.5 \times 10^6$ |
| M-MSV-Balb/3T3 | $2.3 \times 10^6$ | $3.2 \times 10^6$ |

The number A is that obtained by suspending 60 mg of Cytodex-1 (supplied by Pharmacia Co.) in 20 ml of the culture medium according to Manual of Use of Microcarriers (supplied by Pharmacia Co.), inoculating the culture medium with $4\times10^6$ cells and conducting culturing for 5 days.

The number B is that obtained when the cationized granular pellet was used.

Each number is the number of cells adhering to particles contained in 1 ml.

EXAMPLE 4

The washed gel film obtained in Example 1 was cut into a disc having a diameter of 30 mm and heat-sterilized in a proper amount of distilled water at 120° C. for 20 minutes. The sterilized washed gel film was neutralized by a small amount of a solution of NaOH and was placed in (e) a liquid mixture comprising 1 ml of calf fetus serum, 8 ml of Vitrogen 100 (supplied by Collagen Co., U.S.A.) and 1 ml of 10 times-concentrated MEM culture medium or (f) a liquid mixture comprising 1 ml of calf fetus serum, 8 ml of Vitrogen 100 (supplied by Collagen Co., U.S.A.) and 1 ml of 10 times-concentrated Dulbecco's modified MEM culture medium. In this state, the gel film was allowed to stand at 4° C. overnight, and the gel film equilibrated with collagen was placed in a plastic petri dish having a diameter of 30 mm. The collagen was gelled at 37° C. for 10 minutes.

The petri dish [collagen-treated gel film (e)] was charged with 4 ml of an MEM culture medium having $2\times10^5$ L-929 cells suspended therein and containing 10% of calf fetus serum or 4 ml of an MEM culture medium having $2\times10^5$ J-111 cells suspended therein and containing 10% of calf fetus serum, and the petri dish containing the collagen-treated gel film (f) was charged with 4 ml of Dulbecco's modified MEM culture medium having $2\times10^5$ 3T3 Swiss albino cells suspended therein and containing 10% of calf fetus serum or 4 ml of Dulbecco's modified EME culture medium having $2\times10^5$ M-MSV-Balb/3T3 cells suspended therein and containing 10% of calf fetus serum. Stationary culturing was conducted in a carbon dioxide gas incubator at 37° C. for 5 days. After termination of culturing, the collage-treated gel film was taken out and sufficiently washed with phosphate buffer saline, and the film was treated at 37° C. for 20 minutes in a 0.3% solution of trypsin and the cells were peeled from the surface of the collagen-treated gel film by using a rubber policeman. The number of cells in the obtained cell suspension was measured according to the trypan blue dye exclusion test. The results are shown in Table 5.

TABLE 5

Evaluation of Collagen-Treated Gel Film Obtained by Stationary Culture Method

| Cells | A | B | C |
| --- | --- | --- | --- |
| L-929 | $3.6 \times 10^6$ | $0.8 \times 10^5$ | $3.0 \times 10^6$ |
| J-111 | $2.1 \times 10^6$ | $0.8 \times 10^5$ | $2.0 \times 10^6$ |
| M-MSV-Balb/3T3 | $2.6 \times 10^6$ | $0.8 \times 10^5$ | $2.7 \times 10^6$ |
| T3 Swiss albino | $3.0 \times 10^6$ | $0.8 \times 10^5$ | $3.2 \times 10^6$ |

Note
A: the number of cells growing in the plastic petri dish having a diameter of 30 mm
B: the number of cells growing when the washed gel film not treated with collagen was used
C: the number of cells growing in the collagen-treated washed gel film Each number was number of cells per petri dish having a diameter of 30 mm.

EXAMPLE 5

A mixture of 200 g of the washed gel film obtained in Example 1, 200 g of water and 4 g of NaOH was stirred at 80° C. for 2 hours, and 10 g of 2-bromoethylamine hydrobromine was added to the liquid mixture over a period of 30 minutes and reaction was carried out at 80° C. for 6 hours. After termination of reaction, the alkali was neutralized with dilute hydrochloric acid, and the obtained aminoethylated gel film was washed with a proper amount of water.

EXAMPLE 6

A mixture comprising 200 g of the washed gel film obtained in Example 1, 200 g of water and 3.5 g of NaOH was stirred at 80° C. for 1 hour, and 15 g of 2-dimethylaminoethyl chloride hydrochloride and 40 ml of water were added to the liquid mixture and reaction was carried out at 80° C. for 6 hours. After termination of the reaction, the alkali was neutralized with dilute hydrochloric acid, and the obtained diethylaminoethylated gel film was washed with a proper amount of water.

EXAMPLE 7

A mixture comprising the washed gel film obtained in Example 1, 100 g of water and 2 g of NaOH was allowed to stand at 70° C. for 1 hour. Then, 5 g of epichlorohydrin was added to the liquid mixture and the mixture was allowed to stand at 80° C. for 5 hours. The treated gel film was washed and cut into a disc having a diameter of 30 mm. The film was heat-sterilized in distilled water at 120° C. for 20 minutes. Then, 3 ml of Vitrogen 100 (supplied by Collagen Co., U.S.A.), 5 ml of water and 1 ml of 10 times-concentrated MEM culture medium were added to the gel film, and the film was allowed to stand in this state at 40° C. for one day and night to form a covalent bond between the gel cellulose film and collagen.

EXAMPLE 8

The washed gel film (100 g) obtained in Example 1 was added into 1 l of water, and the pH value was adjusted to 11.5 by 10N NaOH. While 20 g of cyanogen bromide was gradually added, 10N NaOH was dropped so that the pH value was not reduced below about 11.5. The reaction was carried out at 30° C. for 1 hour. The obtained activated gel was washed in running water for 3 hours. The activated gel was reacted with a solution of 500 mg of collagen in 10 ml of water at 20° C. for 2 hours. After reaction, the collagen-bonded gel was washed in running water. The gel was immersed in tris-hydrochloric acid buffer having a pH value of 8 at room temperature for 24 hours to block excessive cyanogen bromide. The tris-hydrochloric acid buffer was washed away by running water.

EXAMPLE 9

A mixture comprising 100 g of the washed gel film obtained in Example 1, 100 g of water and 3 g of NaOH was stirred at 60° C. for 1 hour. Then, 100 ml of a 1% aqueous solution of chloro-acetic acid having the pH value adjusted to 12.0 by sodium hydroxide was added to the liquid mixture, and a reaction was carried out at 90° C. for 4 hours. After the reaction, the alkali was neutralized with dilute hydrochloric acid, and the obtained carboxymethylated gel film was washed with a proper amount of water.

EXAMPLE 10

Toxicity and pyrogen tests of the washed gel film obtained in Example 1

In 900 ml of physiological saline solution was immersed 100 g of the washed gel film obtained in Example 1 at 37° C. for 24 hours. The liquid after the immersion was subjected to the following tests. Physiological saline solution before the immersion was used as the control.

(1) Acute Toxicity Test

The sample liquid was intravenously injected in an amount of 50 ml/kg into 10 mice having a body weight of 18 to 21 g. The change of the weight was checked every day for 5 days. No significant difference was observed between the sample liquid and the control.

(2) Pyrogen Test

The sample liquid was intravenously injected in an amount of 10 ml/kg into 3 rabits having a body weight of 1.7 to 1.9 kg. The body temperature was measured 3 times at intervals of 1 hour. Elevation of the temperature was not observed.

(3) Test of Determination of Endotoxin

Endotoxin in the sample liquid was determined by using Pyrodick (reagent for determining endotoxin by the colorimetry; supplied by Seikagaku Kogyo K.K.). Endotoxin was not detected at all.

EXAMPLE 11

Cell-culturing test using gel films obtained in Examples 1, 4, 5, 6, 7, 8 and 9

Each of the gel films obtained in Examples 1, 4, 5, 6, 7, 8 and 9 was cut into a disc having a diameter of 30 mm. The film was heat-sterilized or UV-sterilized at 120° C. for 20 minutes. The sterilized gel film was sufficiently equilibrated with an MEM culture medium containing 10% of calf fetus serum and was placed in a plastic petri dish having a diameter of 30 mm. Then, the petri dish was charged with 4 ml of an MEM culture medium having $2 \times 10^5$ L-929 cells suspended therein and containing 10% of calf fetus serum, and stationary culturing was carried out in a carbon dioxide gas incubator at 37° C. for 5 days. After culturing, the gel film was taken out, washed with phosphate buffer saline and treated in 4 ml of a 0.3% solution of trypsin at 37° C. for 20 minutes. Cells were peeled from the surface of the cationized gel film by using a rubber policeman. The number of cells in the obtained cell suspension was measured according to the trypan blue dye exclusion test. The obtained results are shown in Table 6.

TABLE 6

Culturing of L-929 Cells Using Gel Films Treated by Various Methods

| Treatment of Gel Film | Number of Cells* |
| --- | --- |
| Untreated (washed gel film) | $0.8 \times 10^5$ |
| Collagen treatment (Example 4) | $3.0 \times 10^6$ |
| Collagen crosslinking (Example 7) | $2.8 \times 10^6$ |
| Cationization (Example 1) | $3.2 \times 10^6$ |
| Aminoethylation (Example 5) | $2.5 \times 10^6$ |
| DEAE conversion (Example 6) | $3.0 \times 10^6$ |
| Carboxymethylation (Example 9) | $2.6 \times 10^6$ |
| Collagen crosslinking (Example 8) | $3.0 \times 10^6$ |
| Cationization and collagen treatment** | $3.0 \times 10^6$ |

Note
*: the number of living cells recovered from one gel film having a diameter of 30 mm
**: the cationized gel film obtained in Example 1 was subjected to the collagen treatment according to the method described in Example 3

EXAMPLE 12

A washed gel film, a cationized washed gel film and a cationized and collagen-treated washed gel film were sterilely obtained according to the methods described in Examples 1 and 4. Each microbially-produced cellulose gel film was shaped into a disc having a diameter of 2 cm. Hairs were removed from the back of an SD rat which was 6 weeks old and had a body weight of 250 g. A wound was experimentally formed on the circular skin portion having a diameter of 1 to 2 cm in a depth of about 0.5 to about 1 mm on the average, and the wound was stiched by using a surgical thread, and gauze was applied to the wound. After 10 days, the degree of rebirth of the skin in the wound was examined. Each gel film was superior to the petrolatum gauze used as the control. When the cationized gel film and the cationized and collagen-treated gel film were used, the bonding to the texture of the wounded part was especially good. After 20 days, each film dropped from the skin surface.

EXAMPLE 13

Each of a washed gel film which had been subjected to sterilization, a cationized gel film obtained according to the method described in Example 1 and a collagen-treated cationized gel film obtained in Example 4 was cut into a disc having a diameter of 30 mm and sufficiently equilibrated in Dulbecco's modified MEM culture medium containing 10% of calf fetus serum, and the film was placed in a plastic petri dish having a diameter of 30 mm. The petri dish was charged with 2 ml of Dulbecco's modified MEM culture medium containing 10% of calf fetus serum, in which 3.5×10$^5$ mouse 3T3 cells irradiated with gamma rays at 8,000 roentgens were suspended, and the petri dish was allowed to stand in a carbon dioxide gas incubator at 37° C. for 6 hours. After the culture medium was removed, the petri dish was charged with a culture medium for human epidermal keratinocyte (prepared according to the method of Green et al), which was composed mainly of 2 ml of Dulbecco's modified MEM culture medium containing 10% of calf fetus serum, in which 2×10$^5$ human epidermal keretinocyte cells cultured by the method of Green et al (Howard Green and Olaniyi Kehinde, Proc. Natl. Acad. Sci. USA, 1979, 76, 5665–8) were suspended, and culturing was conducted in a carbon dioxide gas incubator at 37° C. for 5 days. After culturing, the number of human epidermal keratinocyte cells propagated on the gel film was measured by using a microscope. The results are shown in Table 7.

TABLE 7

Culturing of Human Epidemic Keratinocyte Cells by Using Gel Films

| Gel Film | Number of Cells |
| --- | --- |
| Washed gel film | 0.5 × 10$^6$ (0.2 × 10$^6$)* |
| Cationized gel film | 1.2 × 10$^6$ (0.2 × 10$^6$)* |
| Cationized and collagen-treated gel film | 2.5 × 10$^6$ (1.0 × 10$^6$)* |

Note
*: the parenthesized value indicates the number of cells obtained when human epidermal keratinocyte cells were cultured by using the gel film to which gamma ray-irradiated mouse 3T3 cells were not caused to adhere After the cells were cultured for 5 days in the above-mentioned manner to form a substantially monolayer, culturing was further conducted for 10 days. The formation of clear multiple layers was confirmed by microscope observation.

EXAMPLE 14

Each of a washed gel film which had been subjected to sterilization, a cationized gel film obtained according to the method described in Example 1 and a collagen-treated cationized gel film obtained according to the method described in Example 4 was cut into a disc having a diameter of 30 mm, sufficiently equilibrated in Dulbecco's modified MEM culture medium and placed in a plastic petri dish having a diameter of 30 mm. The petri dish was charged with a culture medium for human epidermal keratinocyte [prepared according to the method of Green et al (Howard Green and Olaniyi Kahinde, Proc. Natl. Acad. Sci. USA, 1976, 76, 5665–8)], which was composed mainly of 2 ml of Dulbecco's modified MEM culture medium containing 10% of calf fetus serum, in which 2×10$^5$ or 4×10$^6$ human epidermal keratinocyte cells were suspended. The petri dish was allowed to stand in a carbon dioxide gas incubator at 37° C. for 6 hours to cause the human epidermal keratinocyte cells to adhere to the gel membrane.

TABLE 8

| Gel Film | Number of Cells Adhering to Gel Film | |
| --- | --- | --- |
|  | 2 × 10$^5$* | 4 × 10$^6$* |
| Washed gel film | 0.3 × 10$^5$ | 0.4 × 10$^6$ |
| Cationized gel film | 0.8 × 10$^5$ | 1.8 × 10$^6$ |
| Cationized and collagen-treated gel film | 1.1 × 10$^5$ | 2.5 × 10$^6$ |

Note
*: the number of cells contained in the charged suspension

EXAMPLE 15

The diethylaminoethylated gel film obtained in Example 6 was immersed in a 0.5% aqueous solution of sodium alginate at 50° C. for 3 hours to impregnate the film with sodium alginate. The surface was lightly water-washed to remove excessive sodium alginate. Then, the film was immersed in a 0.1M aqueous solution of calcium chloride at room temperature for 30 minutes, whereby a part of sodium alginate in the diethylaminoethylated gel film was gelled. The film was washed, and in the same manner as described in Example 11, animal cells were cultured. The number of cells growing on the surface was 3.0×10$^6$.

With respect to each of the diethylaminoethylated gel film which was impregnated with sodium alginate and in which sodium alginate was then gelled, the gel film not impregnated with sodium alginate, and a calcium alginate gel formed by gelling a 0.5% aqueous solution of sodium alginate in a 0.1M aqueous solution of calcium chloride, the gel strength was measured by a rheometer. The results are shown in Table 9.

TABLE 9

|  | Gel Strength (g/cm$^2$) |
| --- | --- |
| Diethylaminoethylated gel film impregnated with sodium alginate, followed by gelling | 350 |
| Diethylaminiethgylated gel film | 290 |
| Gel of calcium alginate | 40 |

As is apparent from the foregoing results, if the cyanoethylaminoethylated film was impregnated with sodium alginate and the sodium alginate was then gelled, a good reinforcing effect was attained without an adverse affect on the culturing of animal cells.

EXAMPLE 16

The cationized gel film obtained in Example 1 was immersed in a 7% aqueous solution of polyvinyl alcohol (having an average polymerization degree of 2,000) at 30° C. for 24 hours to impregnate the film with polyvinyl alcohol. The surface of the film was lightly water-washed to remove excessive polyvinyl alcohol. The film was allowed to stand in an atmosphere maintained at −20° C. for 1 hour and then in an atmosphere maintained at ambient temperature to gel a part of polyvinyl alcohol. The film was washed at room temperature, and the culturing of animal cells was carried out in the same manner as described in Example 11. The number of cells growing on the surface was 3.1×10$^6$.

With respect to each of the cationized gel film impregnated with polyvinyl alcohol, followed by gelling, the cationized gel film not impregnated with polyvinyl alcohol and a polyvinyl alcohol gel obtained by allowing a 7% aqueous solution of polyvinyl alcohol alone to stand in an atmosphere maintained at −40° C. for 1 hour and then in an atmosphere maintained at ambient temperature, the gel strength was measured by a rheometer. The results are shown in Table 10.

TABLE 10

|  | Gel Strength (g/cm$^2$) |
| --- | --- |
| Cationized gel film impregnated with polyvinyl alcohol, followed by gelling | 330 |
| Cationized gel film | 285 |
| Gel of polyvinyl alcohol | 25 |

As is apparent from the foregoing results, if the cationized gel film was impregnated with polyvinyl alcohol and polyvinyl alcohol was gelled, a good reinforcing effect was obtained without an adverse affect on the culturing of animal cells.

EXAMPLE 17

With respect to all of six gels, the gel strength of which was measured in Examples 15 and 16, the exudation amount of the liquid component was measured. Namely, each gel was inserted between two filter papers and a pressure of 10 g/cm$^2$ was applied for 10 minutes, and the ratio of the exudated liquid was determined. The results are shown in Table 11.

TABLE 11

|  | Ratio (%) of Exudated to Original Gel |
| --- | --- |
| Diethylaminoethylated gel film impregnated with sodium alginate, followed by gelling | 15 |
| Diethylaminoethylated gel film | 75 |
| Calcium alginate gel | 20 |
| Cationized gel film impregnated with polyvinyl alcohol, followed by gelling | 25 |
| Cationized gel film | 72 |
| Polyvinyl-alcohol gel | 33 |

From the results shown in Table 11, it is seen that if the chemically modified microbe-produced cellulose gel film of the present invention was impregnated with sodium alginate or polyvinyl alcohol, exudation of the liquid component could be prevented.

We claim:

1. A skin graft or vulnerary cover for external wound surfaces, which comprises a complex of a water-containing gel of modified microbially-produced cellulose with human cells bonded to or adsorbed in said gel, said human cells consisting of human epidermal cells, said human epidermal cells being cultured substantially in a monolayer state on the water-containing gel form of the modified microbially-produced cellulose, wherein:

1) an animal cell adhesive protein is physically or chemically bonded to the modified microbially-produced cellulose, or 2) said cellulose contains hydroxyl groups, wherein at least a portion of the hydrogen atoms of the hydroxyl groups are substituted with a positively or negatively charged group, or 3) an animal cell adhesive protein is physically or chemically bonded to the modified microbially-produced cellulose, and the cellulose contains hydroxyl groups, wherein at least a portion of the hydrogen atoms of the hydroxyl groups are substituted with a positively or negatively charged group, wherein the positively charged group has the formula (I) or (II):

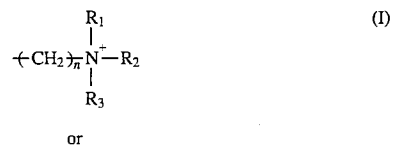

wherein n is an integer of from 0 to 8, and $R_1$, $R_2$ and $R_3$ independently represents a hydrogen atom or an alkyl, aryl, arylalkyl, alkylaryl, cycloalkyl or alkoxyalkyl group, with the proviso that $R_1$, $R_2$ and $R_3$ are not a hydrogen atom simultaneously; and wherein the negatively charged group is selected from the group consisting of a carboxy methyl group, a carboxy ethyl group, a phosphoric acid group and a sulfuric acid group.

2. The skin graft or vulnerary cover of claim 1, wherein the animal cell adhesion protein is selected from the group consisting of collagen, fibronectin, laminin and gelatin.

3. The skin graft or vulnerary cover of claim 1, wherein the chemical bonding is crosslinking through an epihalohydrin or cyanogen bromide.

4. The skin graft or vulnerary cover claim 1, wherein the bonded or absorbed human epidermal cells are anchorage-dependent human epidermal cells.

5. The skin graft or vulnerary cover of claim 1, wherein the microbially-produced cellulose gel has a structure in which ribbon-shaped microfibrils having a width of 100 to 500 Å and a thickness of 10 to 200 Å are entangled with one another.

6. The skin graft or vulnerary cover of claim 1, wherein the gel is complexed with a reinforcing material selected from the group consisting of fabrics, films, paper sheets, porous films selected from the group consisting of polyethylene, polyvinyl alcohol and silicon rubber; granules of alumina, glass and crystalline celluloses; agar, dextran, polyacrylamide, polyvinylpyrrolidone, alginic acid salts, chitin, hyaluronic acid, curdlan, polyacrylic acid salts, pullulan, carrageenan, glucomannan, cellulose derivatives and polyethylene glycol.

7. The skin graft of vulnerary cover of claim 1, wherein:

1) said cellulose contains hydroxyl groups, wherein at least a portion of the hydrogen atoms of the hydroxyl groups are substituted with said positively or negatively charged group, or 2) an animal cell adhesive protein is physically or chemically bonded to the modified microbially-produced cellulose, and the cellulose contains hydroxyl groups, wherein at least a portion of the hydrogen atoms of the hydroxyl groups are substituted with said positively or negatively charged groups.

* * * * *